United States Patent [19]

Lee et al.

[11] Patent Number: 5,266,308

[45] Date of Patent: Nov. 30, 1993

[54] HAIR TREATMENT COMPOSITION

[75] Inventors: G. Jae Lee, Trumbull; Paul Vinski, Ridgefield, both of Conn.

[73] Assignee: Chesebrough-Pond's USA Co., Greenwich, Conn.

[21] Appl. No.: 812,528

[22] Filed: Dec. 20, 1991

[51] Int. Cl.$^5$ .............................. A61K 7/11
[52] U.S. Cl. ........................ 424/71; 424/47; 424/DIG. 1; 424/78.08; 424/78.24
[58] Field of Search ............ 424/70, 401, DIG. 1, 424/71, 72, DIG. 2, 47, 78.08; 525/167

[56] References Cited

U.S. PATENT DOCUMENTS

| | | | |
|---|---|---|---|
| 3,546,008 | 12/1970 | Shields et al. | 117/13.8 |
| 3,734,874 | 5/1973 | Kibler et al. | 260/29.2 E |
| 3,779,993 | 12/1973 | Kibler et al. | 260/755 |
| 3,800,033 | 3/1974 | Flawn et al. | 424/47 |
| 3,927,199 | 12/1975 | Micchelli et al. | 424/47 |
| 4,173,627 | 11/1979 | Madrange | 424/47 |
| 4,300,580 | 11/1981 | O'Neill et al. | 132/7 |
| 4,335,220 | 6/1982 | Coney | 523/414 |
| 4,402,977 | 9/1983 | Grollier et al. | 424/70 |
| 4,525,524 | 6/1985 | Tung et al. | 524/601 |
| 4,859,455 | 8/1989 | Nowak, Jr. et al. | 424/47 |
| 4,871,529 | 10/1989 | Sramek | 424/47 |
| 4,874,604 | 10/1989 | Sramek | 424/47 |
| 4,983,383 | 1/1991 | Maksimoski et al. | 424/70 |
| 4,983,418 | 1/1991 | Murphy et al. | 424/47 |
| 5,021,238 | 6/1991 | Martino et al. | 424/47 |
| 5,094,838 | 3/1992 | Benson et al. | 424/47 |

FOREIGN PATENT DOCUMENTS 1222461 6/1987 Canada.
2098624 11/1982 United Kingdom.

OTHER PUBLICATIONS

Research Disclosure, Jun. 1991, pp. 390–391.
Eastman AO Polymers for Water-Based Hair Spray, Pub. #CB-14, Aug. 1990.

*Primary Examiner*—Thurman K. Page
*Assistant Examiner*—Raj Bawa
*Attorney, Agent, or Firm*—Milton L. Honig

[57] ABSTRACT

A hair treatment composition is provided that includes a water-insoluble, dispersible polymeric resin having a viscosity of less than 2 centipoise at 25° C. when dispersed at 10% in water; a water-soluble polymeric resin having a viscosity greater than 6 centipoise at 25° C. when 10% is placed in water; and a water-soluble polymer of molecular weight greater than about 500,000. Illustrative of the water-insoluble resin is a diglycol/cyclohexanedimethanol/isophthalates/sulfoisophthalates polyester. Preferably the water-soluble polymeric resin is a copolymer of polyvinyl-pyrrolidone and vinyl acetate. The preferred water-soluble polymer is polyvinylpyrrolidone, especially a polymer having molecular weight of around 630,000.

14 Claims, No Drawings

HAIR TREATMENT COMPOSITION

BACKGROUND OF THE INVENTION

1. Field of the Invention

The invention relates to hairspray compositions especially formulated for use in low organic volatile systems.

2. Related Art

Hairspray compositions must meet a number of functional requirements. These include good holding ability and curl retention without giving a harsh, brittle feeling to the hair. Even under humid conditions there must be good hold and curl retention. Another requirement is that the hairspray be capable of being removed upon washing the hair at the time of shampooing. Additionally, the compositions must include the properties of low stickiness, good combing characteristics and a lack of powdering or flaking.

Various resins have been employed in hairspray compositions to achieve the aforementioned desirable properties. Illustrative of such resins are the copolymers of vinyl-pyrrolidone with vinyl acetate available commercially under such trademarks as Luviskol VA 37 E by BASF Corp. and homopolymers of vinylpyrrolidone commercialized under the trademark PVP K-30 by GAF Corporation Typical of this art are disclosures in U.S. Pat. No. 3,800,033 (Flawn et al) and U.S. Pat. No. 4,173,627 (Madrange nee Dermain et al). A higher molecular weight homopolymer of vinyl-pyrrolidone, PVP K-90 Resin trademark of GAF Corporation, is disclosed in U.S. Pat. No. 4,874,604 (Sramek). The aforementioned polymeric resins are of the nonionic variety.

Amphoteric resins have also been extensively employed. These polymers contain cationic radicals derived from monomers such as t-butyl aminoethyl methacrylate as well as carboxyl radicals derived from monomers such as acrylic acid or methacrylic acid. Representative of this group is a product manufactured by the National Starch and Chemical Corp. under the trademark Amphomer identified on product labels by the CTFA name of Octylacrylamide/Acrylates/Butylaminoethyl Methacrylate Copolymers. Use of Amphomer alone or in conjunction with other resins for hairsprays has been reported in U.S. Pat. No. 3,927,199 (Micchelli et al), U.S. Pat. No. 4,402,977 (Grollier et al), U.S. Pat. No. 4,859,455 (Nowak, Jr. et al), U.S. Pat. No. 4,871,529 (Sramek), U.S. Pat. No. 4,983,383 (Maksimoski et al), U.S. Pat. No. 4,983,418 (Murphy et al), U.S. Pat. No. 5,021,238 (Martino et al), GB 2 098 624 (Madrange) and Canadian Patent 1 222 461 (Varco).

Anionic polymeric resins have also been utilized in this art. For instance, U.S. Pat. No. 4,300,580 (O'Neill et al) discloses linear polyesters prepared from isophthalic acid, the sodium salt of 5-sulfoisophthalic acid and diethylene glycol. Eastman AQ Polymers for water-dispersed hairsprays are based on this technology. Other polyester and sulfo substituted polymer systems are described in U.S. Pat. No. 4,525,524 (Tung et al).

Environmental concerns and legislation addressing such concerns have required product reformulations to meet these challenges. Organic solvent-based sprays must, at least in part, now be substituted by water systems Levels of organic propellants present in these water systems must also be adjusted to relatively low levels. With these constraints, certain problems have arisen. Water-dispersed systems are slow to dry. Not only do they result in wetness on the hair but there is also an undesirable coolness sensation that imparts a chill. Quite significantly there is also difficulty in developing the style. Resins formulated in a water-dispersed system have weak holding power.

Some systems such as the Eastman AQ Resins have good setting or holding but removability from hair is quite poor because these resins are not water soluble.

Furthermore, there is the problem of providing a uniform spray particle size with water-dispersed resins. A still further problem is that of improving glossiness to counteract resins that usually tend to dull hair.

Accordingly, it is an object of the present invention to provide a hairspray suitable for water-dispersed systems having improved holding and styling characteristics.

Another object of the present invention is to provide a hairspray composition based on a water-dispersed system that dries fairly quickly and does not impart a wetness or coolness feel to hair or scalp.

A further object of the present invention is to provide a hairspray composition for water-dispersed systems that improves glossiness of the hair.

A still further object of the present invention is to provide a hairspray composition for water-dispersed systems that can be sprayed as relatively uniform particles.

These and other objects of the present invention will become more evident from the following summary and detailed description.

SUMMARY OF THE INVENTION

A hair treatment composition is provided comprising:

(i) a water-insoluble, dispersible polymeric resin having a viscosity of less than about 2 centipoise at 25° C. when 10% is dispersed in water, present in an effective amount for setting hair;

(ii) a water-soluble polymeric resin having a viscosity greater than about 6 centipoise at 25° C. when 10% is placed in water, present in an effective amount to aid removal of the dispersible polymeric resin from hair upon shampooing thereof; and (iii) a water-soluble polymer of molecular weight greater than 500,000.

Hair treatment compositions of this invention are dispersed in water which may contain from 0-50% of a propellant such as dimethyl ether.

DETAILED DESCRIPTION

Now it has been discovered that many of the objects of the present invention can be achieved by using a hair treatment composition that includes a water-insoluble, dispersible polymeric resin having a viscosity of less than 2 centipoise at 25° C. (when dispersed at 10% in water), a water-soluble polymeric resin having viscosity greater than 6 centipoise at 25° C. (when placed at 10% in water), and a water-soluble polymer of molecular weight greater than about 500,000. Each of the three components interacts with the other to provide an overall superior hairspray. The water-insoluble resin provides excellent hold but is of low viscosity. The water-soluble resin has some hold, increases viscosity and, importantly aids in removing the water-insoluble resin from the hair upon shampooing. The third component, a water-soluble polymer of molecular weight greater than 500,000 optimizes the spray particles of the resin combination.

A variety of water-insoluble dispersible polymeric resins may be employed for this invention. Most preferred are polyesters functionalized with a sulfo ($SO_3^-$) group in amounts sufficient to water-disperse the polyester. Illustrative of such resins are Eastman AQ Polymers, especially those having a glass transition temperature ranging from about 25° C. to about 45° C. Most preferred is Eastman AQ 38S which is a polyester identified as an ethylene diglycol/cyclohexanedimethanol-/isophthalates/sulfoisophthalates resin. These polyesters can be derived through esterification of:

(a) at least one dicarboxylic acid;

(b) at least one diol, at least 20 mole percent of this diol component being a poly (ethylene glycol) having a formula $H-(-OCH_2CH_2)_nOH$ wherein n is an integer from 2 to about 10, and (c) at least one difunctional monomer containing a $SO_3M$ group attached to an aromatic nucleus, wherein M is hydrogen or a metal ion such as sodium, lithium or potassium.

Preferably the sulfo-monomer component constitutes at least from about 8 to 45 mole percent of the sum of the moles of components (A) and (C), the acid components and the diol being substantially equimolar.

Amounts of the water-insoluble dispersible polymeric resin will range from about 0.5 to about 10%, preferably from about 1.5 to about 8%, optimally between about 2 and about 6% by weight.

A second component of the present invention is a water-soluble polymeric resin having a viscosity greater than about 6 centipoise when 10% is placed in water. A variety of resins are suitable. Advantageously, this resin is a copolymer of polyvinylpyrrolidone and vinyl acetate. Especially effective is a polymer formed from 70% vinylpyrrolidone and 30% vinyl acetate, commercially available by Luviskol VA 73W sold by the BASF Corporation.

Amounts of the water-soluble polymeric resin may range from about 0.5 to about 10%, preferably from about 1.5 to about 5%, optimally between about 1.6 and about 3.2% by weight.

A third necessary component of the present invention is a water-soluble polymer of molecular weight greater than about 500,000. Illustrative of such substance are the homopolymers of polyvinlypyrrolidone which may be commercially available under the trademark PVP K-90 sold by the GAF Corporation. This material has a molecular weight of about 630,000. The polymer is utilized to control median particle size to a range between 35 and 48 microns, optimally between 42 and 45 microns.

Amounts of the water-soluble polymer of molecular weight greater than about 500,000 may range from about 0.05 to about 1%, preferably between about 0.05 and 0.5%, optimally from about 0.05 to about 0.2% by weight (exclusive of any propellant).

For definitional purposes, the term "water-soluble" refers to any material that has solubility of at least 1 gram per 100 grams of water, i.e. 1%, preferably a solubility of at least 5% by weight. Conversely, the term "water-insoluble" refers to substances that are insoluble at a level of less than 1 gram per 100 grams of water, i.e., less than 1% by weight.

Compositions of the present invention will also include water as a solvent carrier for the resins and other components. Water will be present in amounts ranging from about 10% to about 99%, preferably from about 40% to about 95% by weight.

With certain of the resins it may be necessary to neutralize some acidic groups to promote solubility/dispersibility. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Amounts of the neutralizing agents will range from about 0.001 to about 10% by weight.

The present hairspray compositions may be formulated in aerosol or nonaerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than the hairspray concentrate so that pure propellant is not emitted from the container. Examples of suitable propellants include dimethyl ether, propane, n-butane and isobutane, used singly or admixed. Dimethyl ether is preferred because of its water-solubility up to 35% by weight.

The amount of the propellant gases is governed by normal factors well known in the aerosol art. For hairsprays the level of propellant is generally from about 3% to about 50%, preferably from about 5 to about 45%, optimally about 30% of the total composition.

Including the propellant, it is advantageous that the compositions of the present invention be present in a single phase rather than a two-phase composition.

Small quantities of surfactant ranging anywhere from 0.1 to about 10%, preferably from about 0.1 to about 1%, optimally about 0.3% by weight may be present in the compositions of the invention. The surfactant may be an anionic, nonionic or cationic emulsifier. Particularly preferred are nonionic emulsifiers which are formed from alkoxylation of hydrophobes such as fatty alcohols, fatty acids and phenols. Illustrative of such material is Triton X-100, and isooctyl phenyl polyethoxyethanol.

Resins when deposited upon hair quite often impart dullness Counteraction of the dullness effect may be achieved by incorporating low levels of $C_{10}$–$C_{20}$ fatty alcohol esters. Particularly preferred is cetearyl octanoate. Amounts of these luster imparting agents will range from about 0.001 to about 1%, preferably from about 0.0i to about 0 5%, optimally from about 0.02 to about 0 1% by weight.

Compositions of this invention may contain any other ingredient normally used in hairsprays. These other ingredients may include antifoam agents, proteins, antioxidants, fragrances, antimicrobials and sunscreens. Each of these ingredients will be present in an amount effective to accomplish its purpose.

Hairspray formulations of the present invention may, if desired, be packaged in a pump spray container operated without any organic propellant. Otherwise, the composition may be charged into a suitable pressurizable container which is sealed and then charged with propellant according to conventional techniques.

The following examples will more fully illustrate the embodiments of this invention. All parts, percentages and proportions referred to herein and the appended claims are by weight unless otherwise indicated.

EXAMPLE 1

Hairspray composition typical of the present invention is outlined below.

| Component | Weight Percent |
| --- | --- |
| Water | 90.018 |
| Eastman AQ 38S | 5.775 |
| Luviskol VA 73W | 3.45 |
| Triton X-100 | 0.300 |
| Polyvinylpyrrolidone (K-90) | 0.150 |
| Fragrance | 0.150 |
| Dow Corning 190 SU | 0.100 |
| Cetearyl Octanoate | 0.030 |
| Triethanolamine | 0.025 |
| DL-panthenol | 0.001 |
| Vitamin E Acetate | 0.001 |

EXAMPLE 2

A series of experiments were conducted to evaluate the most effective relative concentrations of the Eastman AQ 38S resin to the Luviskol VA 73 W copolymer. These experiments utilized the following test procedures.

Film "rinsability" was evaluated by placing a clean, dry, 8"×8" glass plate in a fume hood. The sample hairspray was then applied for 10 seconds evenly coating the glass plate throughout. After drying at least 1 hour at room temperature, a visual observation of clarity, color precipitate or separation, and brittle-cracks in the film were noted. A few drops of warm tap water (about 100° F.) were lightly applied onto the plate. Through light finger action the film was caused to lightly dissolve. Texture was noted. A ranking for the samples was then performed according to ease of rinsability (very poor, poor, medium, good, very good) in comparison to available controls.

Film "hardness," a measure of hair hold capability, was evaluated by evenly applying 2-4 grams of concentrate onto another 8"×8"0 glass plate. Samples were allowed to dry overnight to achieve a thick, dry film. Observations of gelling of the film were recorded. Using a sharp-pointed tool, the film was lightly "scratched" upon the glass plate. Observations were then recorded with regard to hardness and brittleness. A ranking was performed in comparison with known controls.

The above tests were performed on the composition of Example 1 except for the stated variations in resin and copolymer. Table I outlines rinsability and hair hold properties as a function of resin to copolymer ratios.

TABLE I

| Composition | Ratio of AQ 38S:PVP/VA | Rinsability | Hair Hold Capability |
| --- | --- | --- | --- |
| I-A | 93:7 | Not rinsable ↑ | Max. hold ↑ |
| I-B | 87:13 | ↑ Min. rinsable | |
| I-C | 80:20 | | |
| I-D | 77:23 | | |
| I-E | 73:27 | | |
| I-F | 67:33 | ↓ | Min. hold |
| I-G | 60:40 | ↓ Max. rinsable | ↓ Too soft |

Composition I-D having a ratio of resin to copolymer of 77:23 exhibited the optimum performance in rinseabilty and hair hold capability. Where the ratio was 93:7, as in composition I-A, the hairspray was not rinsable. On the other hand, when the ratio was lowered to 60:40, the hairspray had maximum rinsability but was too soft in its holding capability. The above evaluations employed glass plate and in vitro hair swatch techniques standard to the industry.

EXAMPLE 3

Experiments were performed to determine conditions for improved medium particle size and for minimization of the % of particles under 10 microns. Table II records the relationship of increasing % PVP K-90 to the particle distribution.

TABLE II

| % K-90 in the Formula Size | Median Particle Size (μm) | % Under 10.5 μm | Observation |
| --- | --- | --- | --- |
| 0.00 | 32.0 | 5.5 | Uncontrollably fine spray |
| 0.05 | 36.8 | 4.4 | |
| 0.10 | 42.4 | 4.2 | ↑ Acceptable Range |
| 0.15 | 43.3 | 3.4 | |
| 0.20 | 44.2 | 3.6 | ↓ |
| 0.25 | 50.4 | 3.4 | Too coarse - clogs valve |
| 0.50 | 75.4 | 1.8 | Too wet |

Results reported in Table II were obtained on a formulation according to Example 1, except for changes in the K-90 polymer. In the absence of PVP K-90, the median particle size was too small to be practicably employed as a hairspray; small particle sizes resulted in a poor application of both resin and copolymer onto the hair thereby adversely affecting hairset. Too small particle size also presents a safety problem with respect to inhalation doses. On the other hand, very large particle sizes interfered with optimum dry/wet feel properties when spray contacted the head.

Optimum results were found at 0.15% PVP K-90 level at concentrate level (exclusive of propellant weight).

Data shown in Table II was collected using a Malvern 2600 cc particle size analyzer with a 300 mm lens. The instrument utilized a Malvern 2600 laser diffraction particle sizer which comprised an optical measurement unit, computer system, application software package, graphics printer and sample cell. The particle sizes were fully controlled by a desk-top computer which ran the application software package, graphics printer and sample cell.

EXAMPLE 4

Experiments reported hereunder evaluate different grades of PVP polymers. Table III outlines particle size for each grade of PVP polymer. Compositions tested in Table III utilized the combination of 77% Eastman AQ 38S and 23% Luviskol VA 73W.

TABLE III

| Formula | PVP | PVP % | Median Particle Size ($\mu$m) | % Under 10.5 $\mu$m |
|---|---|---|---|---|
| A | K-15 | 0.15 | 28.7 | 8.7 |
| B | K-15 | 0.90 | 29.0 | 8.0 |
| C | K-30 | 0.15 | 29.1 | 8.9 |
| D | K-30 | 0.45 | 29.1 | 7.5 |
| E | K-120 | 0.15 | 39.9 | 4.7 |
| F | K-90 | 0.15 | 43.3 | 3.4 |

From Table III it is evident that K-15 (m.w. 10,000) and K-30 (m.w. 40,000), at the same concentration of 0.15%, did not perform as well as K-90 (m.w. 630,000) in providing satisfactory particle size distributions. K-90 and K-120 (m.w. 3-5 million), at the same concentration level, produced similar results; however, K-90 is preferred because the amount of very low micron size particles was less and, therefore, the inhalation danger reduced.

EXAMPLE 5

A variety of alternative materials to the PVP/VA copolymer were evaluated. Some of these materials required anywhere from mild to substantial neutralization with a base to render them water-soluble. These water-soluble resins which were tested are listed below:
1. Amphomer (available from National Starch)—Octylacrylamide/acrylates/butylaminoethylmethacrylates copolymer
2. Resin 28-2930 (available from National Starch)—Vinylacetate/crotonic acid/vinyl neodecanoate copolymer
3. Luviflex VB-45 (available from BASF)—PVP/t-butyl acrylate/MA copolymer 4 GAX 12-513 (available from Henkel)—polyamide
5. GAF ACP-1018 (available from GAF)—vinyl caprolactam/VP/dimethyl aminoethylmethacrylate copolymer
6. Celquat (available from National Starch)—Polyquaternium-4
7. GAF quat 755N (available from GAF)—Polyquaternium-11
8. Shellac (available from William Zinger & Co.)

All of the above resins (properly neutralized), with the exception of shellac, had applicability for use in the present invention as the water-soluble polymeric resin of viscosity greater than 6 centipoise when 10% was placed in water.

The foregoing description and Examples illustrate selected embodiments of the present invention. In light thereof, various modifications will be suggested to one skilled in the art, all of which are within the spirit and purview of this invention.

What is claimed is:
1. An aqueous hair treatment composition comprising:
   (i) a water-insoluble, dispersible polymeric resin having a viscosity of less than about 2 centipoise at 25° C. when 10% is dispersed in water, present in an amount from about 0.5 to about 10% by weight;
   (ii) a water-soluble polymeric resin having a viscosity greater than about 6 centipoise at 25° C. when 10% is placed in water, present in an amount from about 0.5 to about 10% by weight; and
   (iii) a water-soluble polymer which is polyvinylpyrrolidone of molecular weight greater than 500,000 present in an amount from about 0.05 to about 0.2% by weight.
2. A composition according to claim 1 wherein said water-insoluble, dispersible polymeric resin is a polyester formed from a combination of at least one dicarboxylic acid, at least one diol, and at least one difunctional monomer containing a sulfo group on an aromatic nucleus.
3. A composition according to claim 2 wherein said water-insoluble, dispersible polymeric resin is a diglycol/cyclohexanedimethanol/isophthalates/sulfoisophthalates polyester.
4. A composition according to claim 1 wherein said water-soluble polymeric resin is a copolymer of polyvinylpyrrolidone and vinyl acetate.
5. A composition according to claim 4 wherein said copolymer is a 70:30 weight percent respective combination of polyvinylpyrrolidone and vinyl acetate.
6. A composition according to claim 1 wherein said water-soluble polymer with molecular weight greater than about 500,000 is polyvinylpyrrolidone.
7. A composition according to claim 1 further comprising a $C_{10}$–$C_{20}$ fatty acid ester present in an effective amount to provide luster to hair.
8. A composition according to claim 7 wherein said ester is cetearyl octanoate present in an amount from about 0.001 to about 0.5% by weight.
9. A composition according to claim 1 wherein water is present in an amount from about 10 to about 99% by weight.
10. A composition according to claim 1 wherein weight percent ratio of (i) to (ii) ranges from about 87:13 to about 67:33.
11. A composition according to claim 1 wherein said composition when sprayed has spray particles of median particle size from about 35 to about 48 $\mu$m.
12. A composition according to claim 1 wherein less than 8% of spray particles forming said composition have a size under 10.5 $\mu$m.
13. A composition according to claim 1 wherein the polyvinylpyrrolidone has a molecular weight of 630,000.
14. A composition according to claim 13 wherein said water-insoluble, dispersible polymeric resin is a diglycol/cyclohexanedimethanol/isophthalates/sulfoisophthalates polyester and said water-soluble polymeric resin is a copolymer of polyvinylpyrrolidone and vinyl acetate, present in a respective weight percent ratio from about 87:13 to about 67:33.

* * * * *

UNITED STATES PATENT AND TRADEMARK OFFICE
CERTIFICATE OF CORRECTION

PATENT NO.   :   5,266,308
DATED        :   November 30, 1993
INVENTOR(S)  :   Lee et al.

It is certified that error appears in the above-indentified patent and that said Letters Patent is hereby corrected as shown below:

Title page under the "Assignee" Section "Chesebrough-Pond's USA Co.,"

should read -- Chesebrough-Pond's USA Co., Division of Conopco, Inc. --

Signed and Sealed this

Thirty-first Day of May, 1994

*Attest:*

BRUCE LEHMAN

*Attesting Officer*  Commissioner of Patents and Trademarks